United States Patent [19]

Fontanella et al.

[11] 4,022,766
[45] May 10, 1977

[54] PHARMACOLOGICALLY ACTIVE PYRROLODIAZEPINES

[75] Inventors: Luigi Fontanella; Luigi Mariani, both of Milan; Giorgio Tarzia, Rome, all of Italy

[73] Assignee: Gruppo Lepetit S.p.A., Milan, Italy

[22] Filed: Mar. 17, 1975

[21] Appl. No.: 559,093

[30] Foreign Application Priority Data
Mar. 20, 1975 United Kingdom ............ 12388/75

[52] U.S. Cl. .................... 260/239.3 B; 260/326.47; 260/326.31; 260/326.5 J; 260/326.5 L; 424/274

[51] Int. Cl.² ....................................... C07D 487/04

[58] Field of Search ............... 260/326.31, 239 BD, 260/239.3 B

[56] References Cited

UNITED STATES PATENTS

| | | | |
|---|---|---|---|
| 3,202,699 | 8/1965 | Stempel | 260/239 BD |
| 3,534,021 | 10/1970 | Derieg | 260/239 BD |
| 3,682,892 | 8/1972 | Ning et al. | 260/239 BD |
| 3,764,688 | 10/1973 | Swett | 424/274 |

OTHER PUBLICATIONS

Littell et al.; J. Med. Chem.; vol. 8; p. 722 (1965).
Nakanishi et al.; J. Med. Chem.; vol. 16; pp. 214–219 (1973).
Hromatka et al.; Monatsh fur Chemie; vol. 104; p. 704 (1973).

*Primary Examiner*—Donald G. Daus
*Assistant Examiner*—Mary Vaughn
*Attorney, Agent, or Firm*—Theodore Post; C. Kenneth Bjork

[57] ABSTRACT

Compounds of the following formula

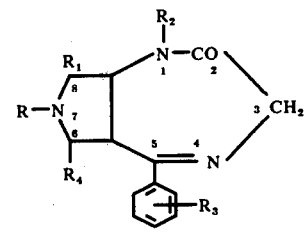

wherein R is hydrogen, methyl, ethyl, propyl, isopropyl, butyl, isobutyl, sec.-butyl or tert.-butyl; $R_1$ is hydrogen, methyl, ethyl or phenyl; $R_2$ is hydrogen, methyl, ethyl, propyl, isopropyl, butyl, isobutyl, sec.-butyl or tert.-butyl; $R_3$ is hydrogen, methoxy, trifluoromethyl, chloro, bromo or fluoro; and $R_4$ is methyl. The new compounds are useful as CNS depressants, anticonvulsants, anti-inflammatories and inhibitors of the enzymes which promote the synthesis of prostaglandins.

6 Claims, No Drawings

PHARMACOLOGICALLY ACTIVE PYRROLODIAZEPINES

This invention refers to pharmacologically active pyrrolodiazepines of the formula I and to the method for their manufacture

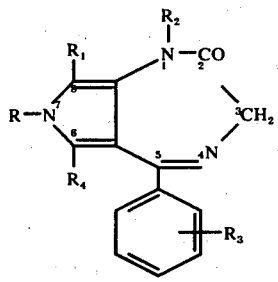

In the formula I the symbol R represents hydrogen, methyl, ethyl, propyl, isopropyl, butyl, isobutyl, sec-butyl and tertbutyl; $R_1$ represents hydrogen, methyl, ethyl and phenyl; $R_2$ represents hydrogen, methyl, ethyl, propyl, isopropyl, butyl, isobutyl, sec-butyl and tert-butyl; $R_3$ represents hydrogen, methoxy, trifluoromethyl, chloro, bromo and fluoro; $R_4$ represents methyl. The new compounds are active as CNS depressants, anticonvulsant, antiinflammatories and inhibitors of the enzymes which promote the synthesis of prostaglandins. 1,4-Diazepines fused with penta- and hexa-atomic heterocyclic rings have already been described in the literature (see for instance Littel et al. J. Med. Chem. 8, 722 (1976); O. Hromatka et al.: Monatsh fur Chemie 104, 704, (1973); M. Nakanishi et al. J. Med. Chem. 16, 214 (1973), but none of these ring systems consists in a 1,4-diazepine condensed with a pyrrole ring. The pyrrolodiazepines of formula I are prepared by cyclization of a 3-benzoyl-4-glycylaminopyrrole derivative of the formula II

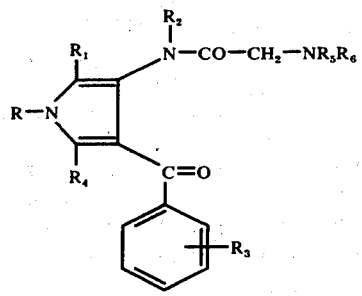

wherein R, $R_1$, $R_2$, $R_3$ and $R_4$ have the same meaning as before and the group —$NR_5R_6$ represents the group amino or a protected amino group such as for instance the phthalimido group. According to the actual practice the derivative II wherein the group —$NR_5R_6$ is a phthalimido rest are preferably employed. The elimination of the phthaloyl moiety and the subsequent intramolecular condensation between the restored amino group and the carbonyl moiety may be actually carried out without isolating the free amino compound (II, $NR_5R_6=NH_2$) as the reaction conditions for the cleavage of the phthalimido group are well suited also for the cyclization step.

This procedure involves refluxing the phthalimido derivatives in a lower alkanol with hydrazine; anhydrous hydrazine excess in a ratio of 3-3,5 molecular proportion is preferably employed. After the lower alkanol is removed, the residue is heated with a strong mineral acid such as hydrochloric acid on a steam bath. After cooling, the phthalhydrazide which forms by cleavage of the phthalimido group, is filtered off and the solution is alkalinized with a dilute alkali hydroxide. The solid which precipitates is collected on filter and then purified by crystallization from lower alkanols. The new pyrrolodiazepine compounds are generally white solids with high melting points, fairly soluble in most of the common organic solvents and in aqueous acidic solutions.

The 3-benzoyl-4-glycylaminopyrrole derivatives II are generally prepared by reaction of a glycyl halogenide of the formula $XCOCH_2$-$NR_5R_6$ wherein X stands for halo and the group $NR_5R_6$ has the same meaning as before, with a 3-benzoyl-4-aminopyrrole of the formula

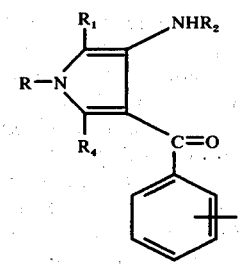

wherein R, $R_1$, $R_2$, $R_3$ and $R_4$ have the same meaning as before. These latter compounds are obtainable by reaction of α-aminonitriles (aminocyanohydrins) of the formula

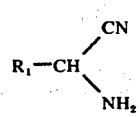

with β-diketones of the formula

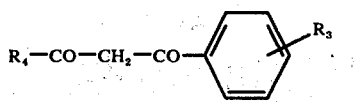

The compound of formula I wherein R and/or $R_2$ are hydrogen may be readily transformed by common alkylation procedures with lower alkyl halides or sulfates into the corresponding compounds wherein R and/or $R_2$ are lower alkyl of 1 to 4 carbon atoms as defined before. The compounds of formula I wherein R and/or $R_2$ represent methyl, ethyl, propyl, isopropyl, butyl, isobutyl, sec-butyl and tert-butyl may also be prepared directly from starting materials of the formula II already containing said lower alkyl groups in the desired position.

Some representative experiments illustrating the anticonvulsant activity of the new compounds are reported in Table I.

TABLE I

Protection against convulsive shock induced by metrazol (pentamethylenetetrazole) in mice

| Compound of Example No. | Dosis administered mg/kg. i.p. | Protected/Treated |
|---|---|---|
| 2 | 100 | 6/10 |
| 3 | 5 | 9/10 |
| 5 | 5 | 6/10 |
| 7 | 100 | 7/10 |
| 9 | 25 | 6/10 |

The methodology followed in performing the experiments summarized above is essentially that described by C. Morpurgo in Arzneim. Forsch. Vol. 21, No. 11, 1727, (1971).

The following Examples further describe the invention and the manner and the process of making and using it without limiting its scope.

EXAMPLE 1

3,7-Dihydro-5,8-diphenyl-6-methyl-pyrrolo[3,4-e][1,4]-diazepine- 2-(1H)-one.

To a solution of 7 g. of anhydrous hydrazine in 350 ml. of methano 27.8 g. of 3-benzoyl-2-methyl-5-phenyl-4-(phthalimidoacetamido)pyrrole are added and the mixture is refluxed for one hour. The solvent is evaporated off and 150 ml. of concentrated hydrochloric acid are added to the residue. After refluxing for one hour the solid precipitated is eliminated by filtration and the filtrate is diluted with water and then alkalinized with 10% sodium hydroxide. The precipitate is crystallized twice from methanol yielding 9 g. of the title product which melts at 310°–12° C.

EXAMPLE 2

3,7-Dihydro-6-methyl-5-phenyl-pyrrolo[3,4-e][1,4]-diazepine-2-(1H)-one.

3-Benzoyl-1-methyl-4-(phthalimidoacetamido)pyrrole (38 g.) is reacted with 6 g. of anhydrous hydrazine in 300 ml. of methanol according to the procedure of the foregoing example. After evaporation of the solvent and refluxing the residue with concentrated hydrochloric acid, the reaction mixture is filtered and the filtrate is alkalinized with dilute sodium hydroxide. The precipitate is crystallized from methanol. Yield 19 g. The compound decomposes at 400° C without melting.

EXAMPLE 3

3,7-Dihydro-6,7-dimethyl-5-phenyl-pyrrolo[3,4-e][1,4]-diazepine-2-(1H)-one.

The compound is obtained according to the procedure of example 1 by employing 3-benzoyl-1,2-dimethyl-4-(phthalimidoacetamido)-pyrrole instead of 3-benzoyl-2-methyl-5-phenyl-4-(phthalimidoacetamido)pyrrole. The compound decomposes at 270° C.

EXAMPLE 4

3,7-Dihydro-5,8-diphenyl-1,6,7-trimethyl-pyrrolo[3,4-e][1,4]-diazepine-2-(1H)-one.

One hundred milligrams of sodium are dissolved in 100 ml. of liquid ammonia and 1.2 g. of 3,7-dihydro-6-methyl-5-phenyl-pyrrolo [3,4-e][1,4]-diazepine-2-(1H)-one are added to the solution. To this mixture 800 mg. of methyl iodide are added with stirring. The ammonia is then evaporated off and 50 ml. of benzene containing 500 mg. of methyl iodide are added to the residue. After heating at 50°–55° C for 1 hour the reaction mixture is cooled and then washed with water. The organic phase is then dried over sodium sulfate and evaporated to dryness giving 600 mg. of the title product. M.p. 232°–4° C (from methanol).

EXAMPLES 5–13

By following the procedure described in Example 1 the following compounds are prepared:

5. 3,7-Dihydro-8-ethyl-6-methyl-5-phenyl-pyrrolo[3,4-e][1,4]-diazepine-2-(1H)-one; from 3-benzoyl-5-ethyl-2-methyl-4-(phthalimidoacetamido)pyrrole. The compound melts at 290° C with decomposition.

6. 3,7-Dihydro-6,7-dimethyl-8-ethyl-5-phenyl-pyrrolo[3,4-e][1,4]-diazepine -2-(1H)-one, from 3-benzoyl-1,2-dimethyl-5-ethyl-4-(phthalimidoacetamido)-pyrrole. The compound melts at 254°–6° C. 7. 3,7-Dihydro-5-(2-chlorophenyl)-6-methyl-pyrrolo[3,4-e][1,4]-diazepine-2-(1H)-one, from 3-(2-chlorobenzoyl)-2-methyl-4-(phthalimidoacetamido)pyrrole. The compound melts at 315° C with decomposition.

8. 3,7-Dihydro-5-(2-fluorophenyl)-6-methyl-pyrrolo[3,4-e][1,4]-diazepine -2-(1H)-one, from 3-(2-fluorobenzoyl)- 2-methyl-4-(phthalimidoacetamido)-pyrrole. The compound does not melt up to 340° C.

9. 3,7-Dihydro-5-(4-methoxyphenyl)-6-methyl-pyrrolo[3,4-e][1,4]-diazepine-2-(1H)-one, from 3-(4-methoxybenzoyl)-2-methyl-4-(phthalimidoacetamido)pyrrole. The compound does not melt up to 340° C.

10. 3,7-Dihydro-7-ethyl-6-methyl-5-phenyl-pyrrolo[3,4-e][1,4]-diazepine-2-(1H)-one, from 3-benzoyl-1-ethyl-2-methyl-4-(phthalimidoacetamido)pyrrole. The compound melts at 229°–31° C.

11. 3,7-Dihydro-6-methyl-5-phenyl-7-propyl-pyrrolo[3,4-e][1,4]-diazepine-2-(1H)-one, from 3-benzoyl-2-methyl-1-propyl-4-(phthalimidoacetamido)pyrrole. The compound melts at 163°–5° C.

12. 7-Butyl-3,7-dihydro-6-methyl-5-phenyl-pyrrole[3,4-e][1,4]-diazepine-2-(1H)-one, from 3-benzoyl-1-butyl-2-methyl-4-(phthalimidoacetamido)pyrrole. The compound melts at 152°–3° C.

13. 3,7-Dihydro-7-isobutyl-6-methyl-5-phenyl-pyrrole[3,4-e][1,4]-diazepine-2-(1H)-one, from 3-benzoyl-1-isobutyl-2-methyl-4-phthalimidoacetamido)pyrrole. The compound melts at 191°–3° C.

EXAMPLES 14–15

By following the procedure of Example 4 the following compounds are prepared:

14. 3,7-Dihydro-5-phenyl-1,6,7-trimethyl-pyrrole[3,4-e][1,4]-diazepine-2-(1H)-one, from 3,7-dihydro-6,7-dimethyl-5-phenyl-pyrrole[3,4-e][1,4]-diazepine-2-(1H)-one and methyl iodide. The compound melts at 237°–9° C.

15. 3,7-Dihydro-6,7-dimethyl-1-ethyl-5-phenyl-pyrrole[3,4-e]-[1,4]-diazepine-2-(1H)-one, from 3,7-dihydro-6,7-dimethyl-5-phenyl-pyrrole[3,4-e][1,4]-diazepine-2-(1H)-one and ethyl iodide. The compound melts at 136°–8° C.

Other compounds of the formula I which may be obtained according to the procedures described above have the following structures:

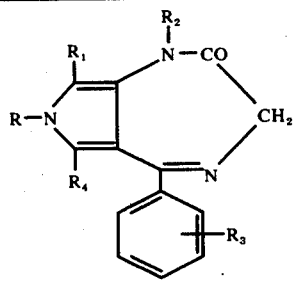

| R | R₁ | R₂ | R₃ | R₄ |
|---|---|---|---|---|
| H | H | C₃H₇ | H | CH₃ |
| CH₃ | C₆H₅ | H | H | CH₃ |
| CH₃ | H | iso C₃H₇ | H | CH₃ |
| CH₃ | CH₃ | H | 2-Br | CH₃ |
| C₂H₅ | C₂H₅ | C₂H₅ | 2-Br | CH₃ |
| C₄H₉ | H | C₄H₉ | 2-CF₃ | CH₃ |
| H | C₂H₅ | H | 3-CF₃ | CH₃ |
| CH₃ | CH₃ | H | 4-Cl | CH₃ |
| H | C₂H₅ | CH₃ | 4-Cl | CH₃ |
| CH₃ | C₆H₅ | H | 3-Br | CH₃ |
| CH₃ | CH₃ | CH₃ | 3-Br | CH₃ |
| C₂H₅ | C₂H₅ | H | 3-CH₃O | CH₃ |
| iso C₄H₉ | H | iso C₄H₉ | 3-CH₃O | CH₃ |
| CH₃ | C₂H₅ | H | 2-CH₃O | CH₃ |
| sec C₄H₉ | H | sec C₄H₉ | H | CH₃ |
| iso C₃H₇ | H | iso CH₃H₇ | H | CH₃ |
| CH₃ | H | H | 3F | CH₃ |
| CH₃ | H | H | 3-Cl | CH₃ |
| CH₃ | H | H | 4-F | CH₃ |
| CH₃ | H | H | 4-Br | CH₃ |

Preparation of intermediates a. 4-Amino-3-benzoyl-2-methyl-5-phenylpyrrole.

2-Amino-2-phenyl-acetonitrile (0.04 mole) and benzoyl acetone (0.04 mole) are refluxed for four hours in 30 ml. of anhydrous benzene in the presence of 100 mg. of p-toluenesulfonic acid. After cooling the reaction mixture is filtered and the solvent is evaporated off to give an oily residue which is dissolved in an ethanol solution containing sodium ethoxide (0.041 mole) and the mixture is allowed to stand for 12 hours at the room temperature. The solid precipitate which forms is recovered by filtration.

Yield 70%. M.p. 203°–5° C.

b. 3-Benzoyl-2-methyl-5-phenyl-4-(phthalimidoacetamido)-pyrrole.

4-Amino-3-benzoyl-2-methyl-5-phenylpyrrole (22.4 g.) is dissolved in 1400 ml. of chloroform and 160 ml. of 1N sodium hydroxide are added to the mixture. By keeping the temperature at 0°–5° C, 17.6 g. of phthalimidoacetyl chloride in 120 ml. of chloroform are added with stirring. After one hour the reaction mixture is cooled and the solid precipitated is recovered on filter and then crystallized from ethanol. Yield 27.8 g.; M.p. 288°–90° C.

c. 3-Benzoyl-2-methyl-4-(phthalimidoacetamido)-pyrrole.

The compound is obtained according to the procedure described above by employing 4-amino-3-benzoyl-2-methylpyrrole as the starting material. The compound decomposes at 260° C.

d. 3-Benzoyl-1,2-dimethyl-4-(phthalimidoacetamido)pyrrole.

The compound is obtained by alkylating 3-benzoyl-2-methyl-4-(phthalimidoacetamido)pyrrole with one equivalent amount of methyl iodide in the presence of sodamide in liquid ammonia. M.p. 224° C (from methanol.)

By following substantially the same procedures described above the following intermediates of formula II have been prepared. 3-benzoyl-5-ethyl-2-methyl-4-(phthalimidoacetamido)pyrrole. M.p. 298°–300° C.

3-Benzoyl-1,2-dimethyl-5-ethyl-4-(phthalimidoacetamido)pyrrole. M.p. 245°–7° C.

3-(2-Chlorobenzoyl)-2-methyl-4-(phthalimidoacetamido)pyrrole. M.p. 220°–3° C.

3-(2-Fluorobenzoyl)-2-methyl-4-(phthalimidoacetamido)pyrrole. M.p. 265°–7° C.

3-(4-Methoxybenzoyl)-2-methyl-4-(phthalimidoacetamido)pyrrole. M.p. 243–5° C.

3-Benzoyl-1-ethyl-2-methyl-4-(phthalimidoacetamido)pyrrole. M.p. 176°–8° C.

3-Benzoyl-2-methyl-1-propyl-4-(phthalimidoacetamido)pyrrole. M.p. 169°–71° C.

3-Benzoyl-1-butyl-2-methyl-4-(phthalimidoacetamido)pyrrole. M.p. 163°–5° C.

3-Benzoyl-1-isobutyl-2-methyl-4-(phthalimidoacetamido)pyrrole. M.p. 220°–2° C.

We claim:

1. A compound of the formula

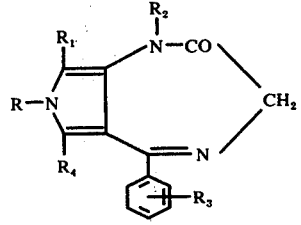

wherein the symbol R represents one of hydrogen, methyl, ethyl, propyl, isopropyl, butyl, isobutyl, sec-butyl and tert-butyl; R₁ represents one of hydrogen, methyl, ethyl and phenyl; R₂ represents one of hydrogen, methyl, ethyl, propyl, isopropyl, butyl, isobutyl, sec-butyl and tert-butyl; R₃ represents one of hydrogen, methoxy, trifluoromethyl, chloro, bromo and fluoro; and R₄ represents methyl.

2. The compound of claim 1 which is 3,7-dihydro-6-methyl-5-phenylpyrrolo[3,4-e][1,4]-diazepine-2-(1H)-one.

3. The compound of claim 1 which is 3,7-dihydro-6,7-dimethyl-5-phenyl-pyrrolo[3,4-e][1,4]-diazepine-2-(1H)-one.

4. The compound of claim 1 which is 3,7-dihydro-8-ethyl-6-methyl-5-phenyl-pyrrolo[3,4-e][1,4[-diazepine-2-(1H)-one.

5. The compound of claim 1 which is 3,7-dihydro-5-(2-chlorophenyl)-6-methyl-pyrrolo[3,4-e][1,4]-diazepine-2-(1H)-one.

6. The compound of claim 1 which is 3,7-dihydro-5-(4-methoxyphenyl)-6-methyl-pyrrolo[3,4-e][1,4]-diazepine-2-(1H)-one.

* * * * *